(12) United States Patent
Golovanevsky et al.

(10) Patent No.: US 9,546,946 B2
(45) Date of Patent: Jan. 17, 2017

(54) METROLOGY TARGET INDENTIFICATION, DESIGN AND VERIFICATION (71) Applicant: KLA-Tencor Corporation, Milpitas, CA (US)

(72) Inventors: Boris Golovanevsky, Haifa (IL); Noam Sapiens, Cupertino, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 162 days.

(21) Appl. No.: 14/361,610

(22) PCT Filed: Mar. 28, 2014

(86) PCT No.: PCT/US2014/032248
§ 371 (c)(1),
(2) Date: May 29, 2014

(87) PCT Pub. No.: WO2014/160976
PCT Pub. Date: Oct. 2, 2014

(65) Prior Publication Data
US 2015/0233814 A1    Aug. 20, 2015

Related U.S. Application Data (60) Provisional application No. 61/806,053, filed on Mar. 28, 2013.

(51) Int. Cl.
| | |
|---|---|
| *A61F 11/06* | (2006.01) |
| *G10K 11/16* | (2006.01) |
| *H03B 29/00* | (2006.01) |
| *G01N 21/01* | (2006.01) |
| *G01N 21/95* | (2006.01) |

(52) U.S. Cl.
CPC .......... *G01N 21/01* (2013.01); *G01N 21/9501* (2013.01); *G01N 2201/025* (2013.01)

(58) Field of Classification Search
CPC ................ G10N 21/01; G10N 21/9501; G10N 2201/025
USPC .......................................... 381/71.2; 356/244
See application file for complete search history.

(56) References Cited

U.S. PATENT DOCUMENTS

| | | |
|---|---|---|
| 5,710,396 A | 1/1998 | Rogers |
| 5,823,307 A | 10/1998 | Schubert et al. |
| 5,899,443 A | 5/1999 | Su |
| 6,110,985 A | 8/2000 | Wheeler |

(Continued)

FOREIGN PATENT DOCUMENTS

| | | |
|---|---|---|
| EP | 0478196 A1 | 4/1992 |
| EP | 0772958 A1 | 5/1997 |

(Continued)

*Primary Examiner* — Paul S Kim
(74) *Attorney, Agent, or Firm* — Simpson & Simpson, PLLC (57) ABSTRACT

Metrology tools are provided, which comprise both active and passive vibration isolation devices, passive or active isolation systems such as constrained layer dampers, particle impact dampers or liquid impact dampers, and/or noise cancellation transducers, combined in different supporting structures of the metrology tool to dampen and reduce vibrations at a wide range of frequencies and intensities, and to which frequency range spectral analysis and optimization may be applied to determine specific tool configurations according to the provided principles.

16 Claims, 7 Drawing Sheets

(56) References Cited

U.S. PATENT DOCUMENTS

| | | |
|---|---|---|
| 6,378,672 B1 | 4/2002 | Wakui |
| 6,598,717 B1 | 7/2003 | Wang et al. |
| 7,398,964 B2 | 7/2008 | Knowles et al. |
| 7,502,103 B2 | 3/2009 | Plug et al. |
| 7,726,452 B2 | 6/2010 | Kraner |
| 8,231,098 B2 | 7/2012 | Ryaboy et al. |
| 2002/0101135 A1 | 8/2002 | Giovanardi et al. |
| 2005/0224687 A1 | 10/2005 | Heertjes et al. |
| 2011/0180160 A1 | 7/2011 | Froehlich et al. |
| 2012/0242969 A1* | 9/2012 | Van Der Pasch ... G03F 7/70775 355/72 |

FOREIGN PATENT DOCUMENTS

| | | |
|---|---|---|
| EP | 1092102 A4 | 11/2004 |
| WO | 9604772 A1 | 2/1996 |
| WO | 9827799 A1 | 6/1998 |
| WO | 9927275 A1 | 6/1999 |
| WO | 9958872 A1 | 11/1999 |
| WO | 0242854 A2 | 5/2002 |
| WO | 2013014503 A1 | 1/2013 |

\* cited by examiner

METROLOGY TARGET INDENTIFICATION, DESIGN AND VERIFICATION

CROSS-REFERENCE TO RELATED APPLICATIONS

This application is a Continuation of International Patent Application Serial No. PCT/US2014/32248, filed on Mar. 28, 2014, which application claims priority of U.S. Provisional Patent Application No. 61/806,053, filed on Mar. 28, 2013, which applications are incorporated herein by reference.

FIELD OF THE INVENTION

The present invention relates to the field of vibration damping systems, and more particularly, to vibration damping in metrology tools.

BACKGROUND OF THE INVENTION

U.S. Pat. No. 7,502,103, incorporated herein by reference in its entirety, teaches dampening stage vibrations by implementing a moving counter mass approach. With advancing metrology technology, this approach becomes less cost effective and requires increasing space to accommodate the moving masses.

BRIEF SUMMARY OF THE INVENTION

One aspect of the present invention provides a metrology tool comprising both active and passive vibration isolation devices.

An additional aspect of the present invention provides a method comprising combining at least one active vibration isolation device and at least one passive vibration isolation device into a metrology tool.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

With specific reference now to the drawings in detail, it is stressed that the particulars shown are by way of example and fir purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Metrology tools are provided, which comprise both active and passive vibration isolation devices. Metrology tools may comprise passive isolation system such as constrained layer dampers, particle impact dampers or liquid impact dampers, and/or noise cancellation transducers, combined in different supporting structures of the metrology tool to dampen and reduce vibrations at a wide range of frequencies and intensities. Frequency range spectral analysis and optimization may be applied to determine specific tool configurations according to the provided principles.

The presented tools and methods isolate the tools from the surrounding noise and/or vibrations and reduce the impact of the tools on their surroundings. The isolation system may be designed and optimized to isolate the more sensitive equipment like the scanner from the metrology tool while keeping the metrology tool isolated from environment. The present invention discloses optimized combinations of active and passive vibration damping mechanisms which are designed to face the challenge of the increasing moving masses in metrology tools in a cost effective way. A number of different technologies are tailored according to respective frequency ranges with respect to specific applications. Certain embodiments of the present invention provide isolation solutions for metrology tools which both isolate the metrology system from the environment and isolate the environment from the metrology systems. The solutions provide vibration isolation and vibrational energy dissipation in a cost effective and scalable manner.

Figure 1:
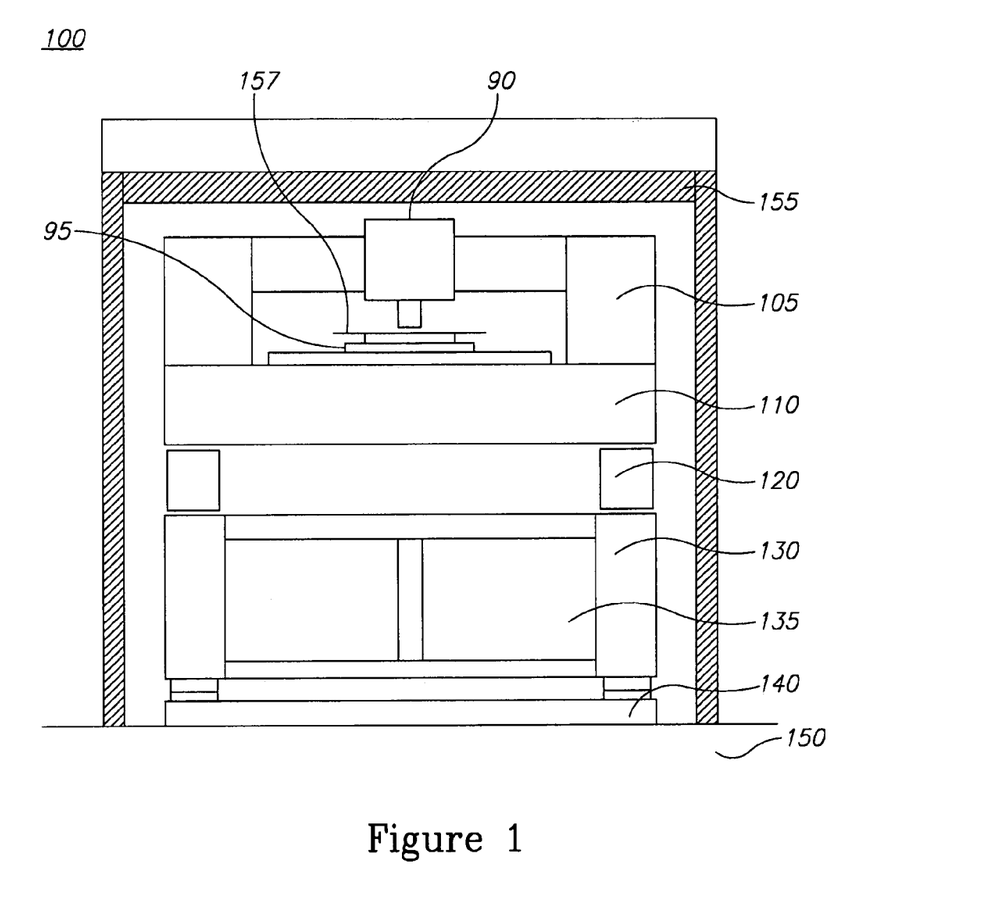
FIG. 1 is a high level schematic illustration of a metrology tool layout, according to some embodiments of the invention.

FIG. 1 is a high level schematic illustration of a metrology tool layout 100, according to some embodiments of the invention. Tool 100 comprises optics 90, stage 95, wafer chuck 157, optics-supporting structure 105, a tool base table 110 (e.g., an optics bench including chuck and wafer stage), an isolation system 120, a tool bench 135, tool bench supports 130 and a pedestal 140 (or floor 150).

While present metrology tools generally use active or passive isolation systems 120, metrology tool 100 combines both active and passive isolation systems 120 as well a passive isolation elements in tool bench supports 130 and in pedestal 140 (or in floor 150).

Figure 2A:
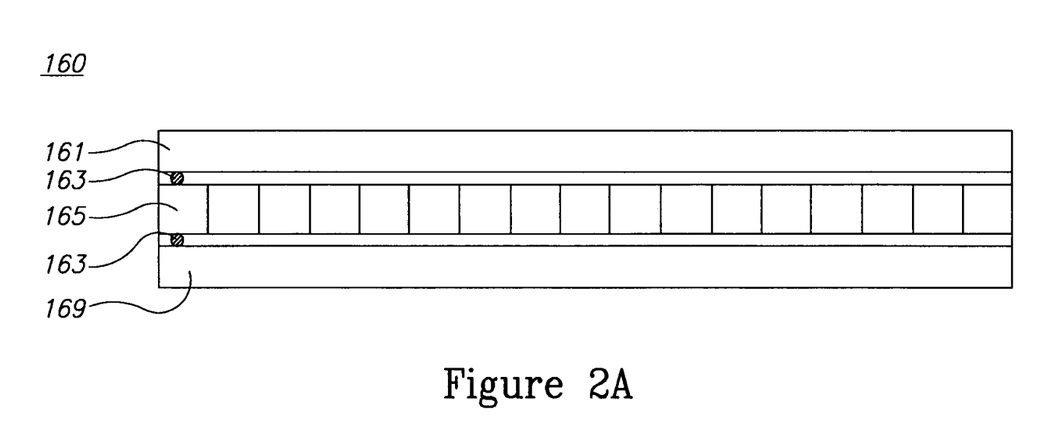
FIG. 2A is a high level schematic illustration of a constrained-layer damping system, according to some embodiments of the invention.
Figure 2B:
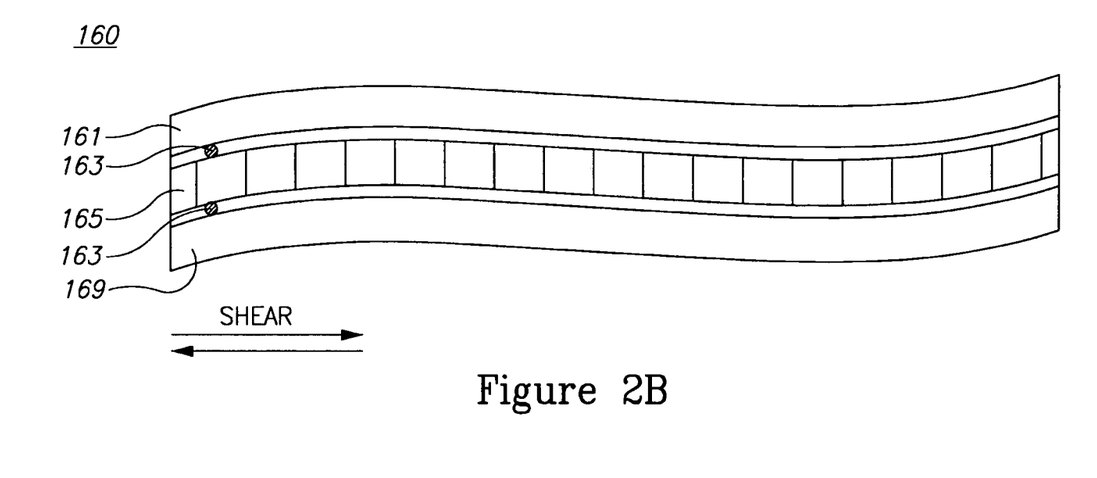
FIG. 2B is a high level schematic illustration of a constrained-layer damping system, according to some embodiments of the invention.

FIGS. 2A and 2B are high level schematic illustrations of a constrained-layer damping system 160, according to some embodiments of the invention. System 160 comprises a damping layer 165 attached (e.g., by adhesive 163) to constraining layers 161, 169. FIG. 2A schematically illustrates system 160 in rest, without applied forces, while FIG. 2B schematically illustrates system 160 under application of horizontal shear forces. Damping layer 165 operates to mild the effect of the shear forces on containing layers 161, 169. Energy is dissipated as a result of shear deformation of damping layer 165 and the resulting extension and compression of the material under flexural stress applied by basal constraining layer 169.

Constrained layer damping means 160 may comprise embedded viscoelastic layer(s) 165 in a structural material. Shear deformation of viscoelastic layer 165 provides energy dissipation and effective damping for natural frequency of the supporting structure.

Figure 3:
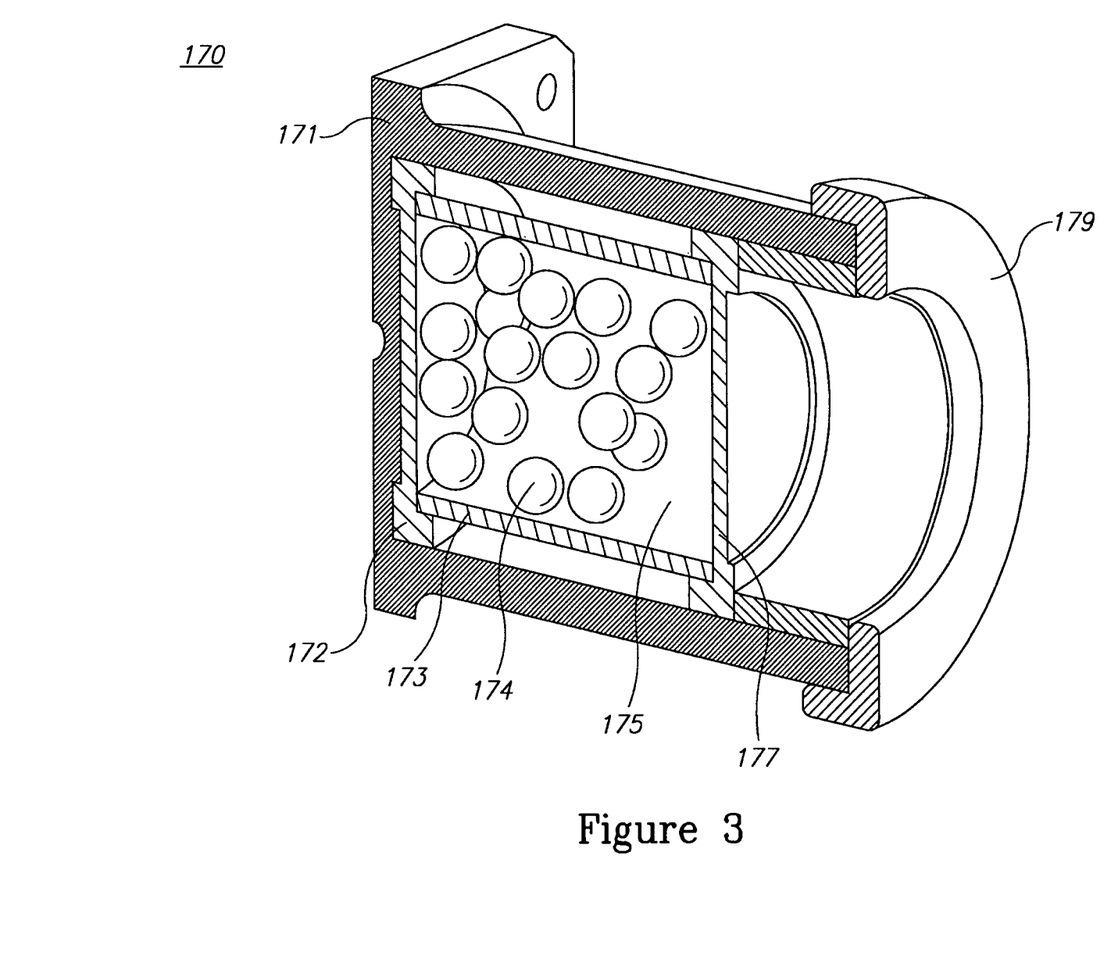
FIG. 3 is a high level schematic illustration of a particle damper, according to some embodiments of the invention.

FIG. 3 is a high level schematic illustration of a particle damper 170, according to some embodiments of the invention. Particle damper 170 comprises particles 174 within an enclosure 175 that is constrained by walls 173, base 172 and cover 177, which are enclosed within housing 171 supporting base 172 and walls 173 and a cap 179 covering housing 171 and configured to transmit applied forces onto cover 177. Vibratory energy in particle damper 170, originating e.g., from the stage movement as part of optics-supporting structure 105, or vibrations from floor 150, is transmitted into granular material 174 and dissipated within it. Without being bound by theory, particle impact dampers 170 dissipate energy through the friction caused by motion of particles 174 within the enclosure defined by walls 173, base 172 and cover 177 and deformation of particles 174 themselves. Some of the volume inside the metrology platform supporting structure 105 or other parts of tool 100 may be partially filled with particles 174 such as sand, ceramics, plastic or metal beads, or any mixture/combination of them.

In certain embodiments, granular material 174 may be replaced by a viscous liquid to provide a liquid-based particle damper 170. Particle damper 170 is a cost effective way to dissipate energy over a broad range of frequencies and temperatures. Particle damper 170 provides damping of stage created shocks and high-g load absorption. Particle damper 170 may be designed to suppress (dampen) the natural frequencies of isolation system 120, structure 105 and/or tool 100 or parts thereof (similarly to the action of a Tuned Mass Damper, TMD). Particle damper 170 may be designed to suppress (dampen) several natural frequencies existing in tool 100 (and thus act like a number of TMDs).

Passive isolation system 120 may be configured to comprise shear layer constrained-layer damping elements 160 (FIG. 2) or/and particle damper 170 or viscous-liquid dampers (FIG. 3). Any supporting structure like optic-supporting structure 105, tool base table 110, tool bench 135, tool legs 130 and levelers and pedestal 140 may comprise shear layer damping elements 160 and or particle damper 170 or viscous-liquid dampers embedded in respective specially designed cavities.

Tool 100 may comprise a combination of passive isolation system 120 such as constrained layer damping 160 in supporting structure 105, and particle dampers (or liquid impact dampers) 170 in supporting structure 105 and/or in tool bench 135, tool legs 130 or pedestal 140 (or floor 150). Such combination provides vibrational damping in a wide dynamic range and good transmissibility for vibration isolation system.

Particle damper 170 or liquid impact dampers may be arranged to absorb or dissipate a part of the stage impact energy to reduce the energy that has to be handled by passive isolation system 120 (comprising e.g., constrained-layer damping elements 160) and/or the energy transferred to the environment.

Figure 4:
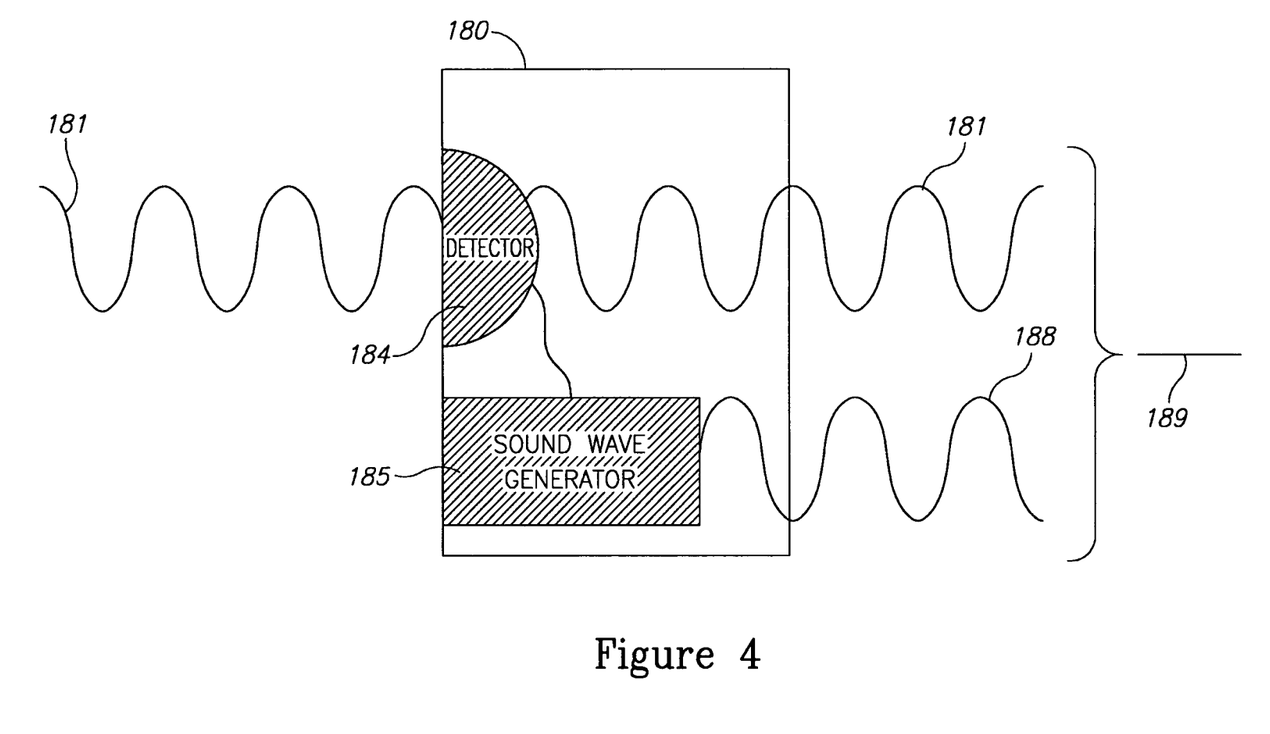
FIG. 4 is a high level schematic illustration of the principle of operation of a noise cancellation transducer, according to some embodiments of the invention; and, FIG. 5 is a high level flowchart illustrating a method, according to some embodiments of the invention.

FIG. 4 is a high level schematic illustration of the principle of operation of a noise cancellation transducer 180, according to some embodiments of the invention. Tool 100 may further comprise noise cancellation transducers 180 to reduce an even larger range of mechanical frequencies. Noise cancellation transducers 180 effectively cancel mechanical noise of any origin (e.g., air, floor, structure) if it resides in their spectral response range.

Noise cancellation transducers 180 are configured to detect (via a detector 184) an input sound wave 181 (noise, vibrations or other) and generate (via a generator 185) an identical sound wave with reversed polarity 188 (having a negative sign, anti-phase, 180° phase difference). Vibration or noise sound wave 181 and induced (device generated) sound wave 188 interfere and cancel each other resulting in a zero (or very close to zero) vibration/noise/sound wave 189. This technique is limited to the frequency and amplitude response of both detection device 184 and inducer 185 of the negative sound wave device. Multiple transducers 180 may be deployed in synchronization to generate broader frequency response (e.g., the interference pattern from multiple sources may be used to generate a more elaborate cancellation pattern). It is noted that sound waves 181 and 189 are depicted in FIG. 4 as pure sine wave for simplicity and illustration purposes only, and in a non-limiting manner, as usually more complicated inputs 181 and cancellation waves 189 are expected). Advantageously, noise cancellation transducers 180 widen the dynamic range and improve the transmissibility for vibration isolation system.

In a non-limiting example, the following aspects may be taken into consideration. Any of these aspects may be combined or adapted to specific conditions.

Passive isolation with low resonance frequency may be associated with or provided on top of, beneath or within pedestal 140, to reduce impact of tool 100 on the environment and isolate tool 100 from environment. For example, the working frequency range of pedestal passive isolation may be chosen to be within the range of 0.5 Hz to 100 Hz or 150 Hz. For example, the passive isolation may be based on isolation based on a negative stiffness effect.

Tool bench 135 is configured to be stiff and massive, with relatively loose mechanical tolerances. Viscoelastic layers (e.g., shear layer constrained-layer damping elements 160) may be embedded into tool bench 135 to dampen relatively high frequencies, for example within a range from 50 Hz up to 1 KHz. The mass of tool bench 135 may be configured to act as low pass filter.

One or more of particle damper 170 (particle-based or liquid-based) may be designed to be set within the internal space of tool bench supports ("legs") 130, in place of or in combination with tuned mass damper(s), TMD). Specifically, the embedded impact damper 170 and/or TMDs may be tuned with respect to a few specific resonant frequencies that should be effectively dampened. In certain embodiments, particle damper 170 may be configured to dampen vibrations within a specified frequency range and additional TMDs may be tuned to certain specific frequencies within or outside the specified frequency range. The specified frequency range may be relative high and may extend up to a few kHz (e.g., 1-10 kHz).

Isolation system 120 may be designed as an active isolation system to comprise mechanical, pneumatic and/or hydraulic springs and motors to reduce the impact of stage 95 on tool 100 and its environment, as well as to isolate stage 95 and tool 100 from the environment. Hence, isolation system 120 may be designed to handle vibrations from any or both stage 95 and floor 150. Active isolation system 120 may be configured to handle vibration frequencies with a range between 2-3 Hz and 100-150 Hz.

Tool base table 110, which is designed to be stiff and massive (made e.g., of granite), may comprise pockets in which a particle damper 170 (particle-based or liquid-based) and/or TMDs are incorporated. These may be configured to dampen vibration over specified frequency ranges and/or at specific resonant frequencies. The frequency ranges may be relatively high and may extend up to a few kHz (e.g., 1-10 kHz). The mass of tool base table 110 may be configured to act as low pass filter.

Optics supporting structure 105, which is configured to be stiff and have tight mechanical tolerances, may incorporate structural damping elements such as damping layers and/or shear layer constrained-layer damping elements 160 and/or structural damping devices like D-strut devices which are characterized by very tight mechanical tolerances and static stiffness.

Tool 100 may be further isolated from the environment, e.g., from acoustic vibrations, by acoustic skins 155 having acoustic pad isolation and active suppression of acoustic noise, using, for example, noise cancellation transducers 180. Acoustic transducers such as noise cancellation transducers 180 may be located on skins 155, tool frame, tool base table 110, tool bench 135 or on supporting structures such as tool bench support 130 and optics supporting structure 105.

Tool stage 95 may comprise one assembly for all axes (X, Y, Z, T) or comprise a distributed system with separate optic moving axes and wafer moving axes. Wafer chuck 157 may comprise with integrated vertical actuators (actuators may comprise, e.g., voice coil, different types of piezo motors, etc.) for active chuck leveling control during the measurements, especially during stage settling time. Chuck subsystem 157 may comprise actuators to control Z/tip/tilt and sensors like gyro and accelerometers to provide the required input. Ire addition, stage feed forward signal is required and incorporated into the actuators' control system. The sensors may be installed on the system element that defines the optical axis (e.g., the main objective) in order to insure perpendicularity between wafer chuck 157 and the optical axis of the measurement head. The actuators may be controlled to maintain or control horizontal wafer position (or the perpendicularity between wafer and optical axis) during all measurement process and thus reduce the MAM (Move—Acquire—Measure) by minimizing waiting time during the settling stage of 95.

Advantageously, while documents such as U.S. Pat. No. 7,502,103 teach dampening stage vibrations by implementing a moving counter mass approach, the present invention does not require using additional moving masses to balance out stage movements.

Hence, the present invention provides a simpler and more reliable solution which is more cost-effective and is less spacious. The disclosed comprehensive hybrid vibration isolation system, having active and/or passive components, provides cost effective, space-effective metrology tool isolation system, by combining and implementing a number of different techniques in the appropriate locations in tool 100. Specific configurations may be adapted to requirements with respect to the analysis of the distribution of vibration frequencies throughout tool 100 and its environment, which was presented above.

Figure 5:
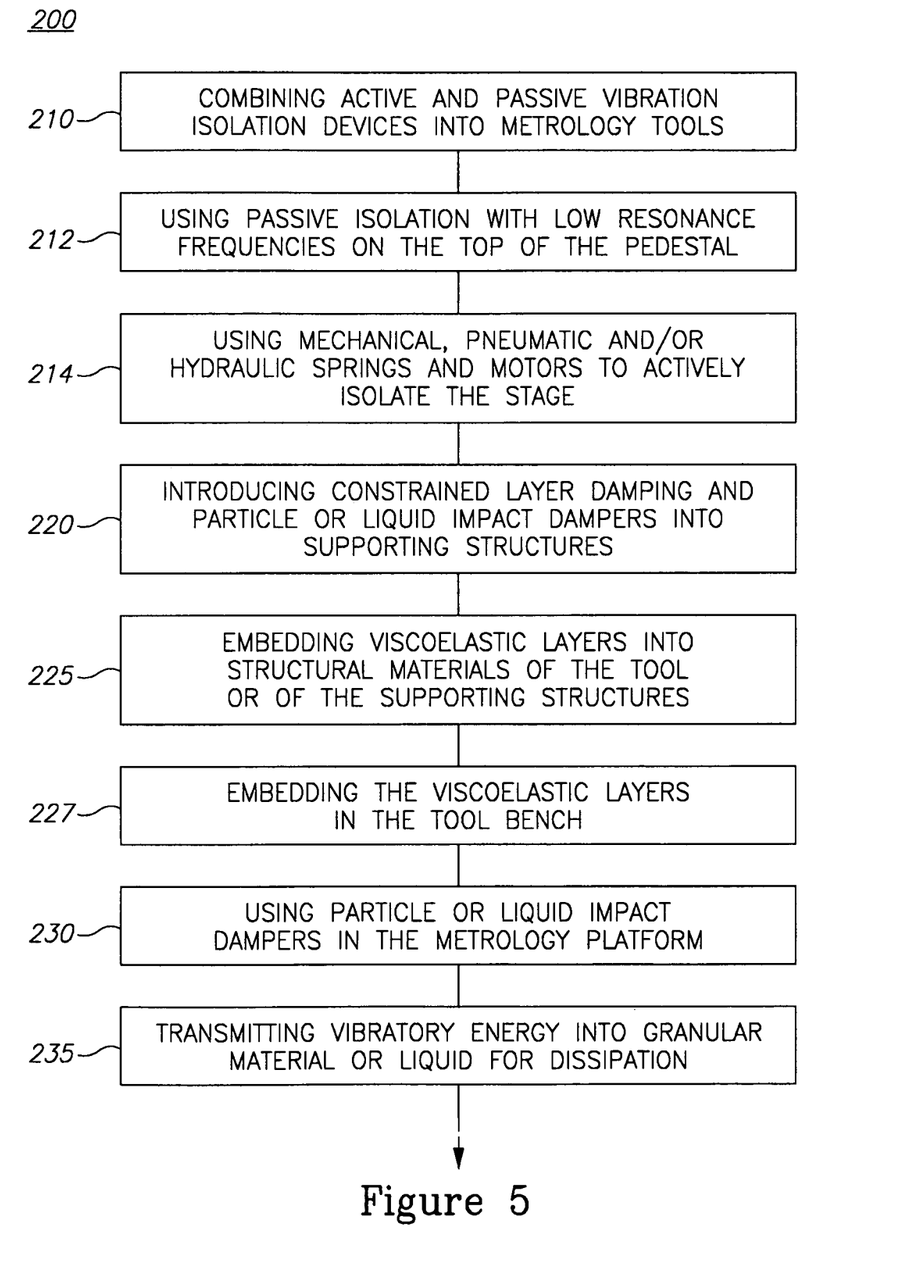

FIG. 5 is a high level flowchart illustrating a method 200, according to some embodiments of the invention. Method 200 may comprise stages for producing, preparing and/or using metrology tool 100, such as any of the following stages, irrespective of their order.

Method 200 comprises combining active and passive vibration isolation devices into metrology tools (stage 210). Method 200 may comprise introducing constrained layer damping and particle or liquid impact dampers into the supporting structure (stage 220) and/or embedding viscoelastic layers into structural materials of the tool or the supporting structures (stage 225) and/or using of particle or liquid impact dampers in the metrology platform (stage 230) to transmit vibratory energy into granular material or liquid for dissipation (stage 235) and/or fitting noise cancellation transducers to reduce mechanical frequencies (stage 240) by cancelling noise through detection the vibration wave and generation of an opposite wave having reversed polarity (stage 245).

Method 200 may further comprise any of the following stages: Using passive isolation with low resonance frequencies on the top of the pedestal (stage 212), using mechanical, pneumatic and/or hydraulic springs and motors to actively isolate the stage (stage 214), embedded the viscoelastic layers in the tool bench (stage 227), incorporating dampers, tuned to specified frequency ranges, within tool bench supports and/or within the tool base table (stage 236), and incorporating damping layers, designed to have tight mechanical tolerances and static stiffness, within the optics' supporting structure (stage 238).

Method 200 may further comprise applying acoustic skins with active suppression of acoustic noise to isolate the stage (stage 247) and applying acoustic transducers to the tool base table and/or to the optics' supporting structures (stage 248) as well as possibly to other supporting structures.

Method 200 may further comprise providing active chuck leveling (stage 250), for example by integrating actuators in the wafer chuck (stage 252) and/or controlling the actuators via sensor data to maintain horizontal wafer position and minimize stage settling waiting time (stage 254).

Any configuration of the stages disclosed above may be adjusted to allow avoiding the moving counter mass approach by configuring the combination of passive and active isolation components to reduce vibrations applied to and acted by the stage (stage 260).

Advantageously, disclosed tools 100 overcome the current limitations in damping vibrations near to natural frequencies of components of tool 100, limitations in transmissibility function of isolation system, limitations in dynamic range, limitations in energy dissipation, as well as attenuating the transfer of most of the stage impact to the floor. The disclosed invention overcomes current challenges of limited dynamical ranges and low degree of energy dissipation of vibration damping elements in metrology tools, and furthermore of damping component natural frequencies and of insufficient transmissibility functions. Disclosed solutions handle the bidirectional transfer of vibrations—from the environment to the stage as well as from the stage to the environment, and thus provides a full and adjustable vibration damping solution.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A metrology tool comprising:
   at least one active vibration isolation device; and,
   at least one passive vibration isolation device, wherein at least one of the at least one active vibration isolation devices or at least one passive vibration isolation devices, is selected from a group consisting of:
   A) a constrained layer damper and at least one particle or liquid impact damper within a supporting structure of the metrology tool;
   B) at least one noise cancellation transducer arranged to reduce mechanical frequencies by cancelling noise;
   C) at least one noise cancellation transducer arranged to detect a vibration wave and generate an opposite wave having reversed polarity;
   D) at least one acoustic skin with at least one noise cancellation transducer configured to isolate the tool from acoustic vibrations in an environment of the tool;
   E) at least one acoustic transducer applied to at least one of a tool base table and optics' supporting structures; and,
   F) combinations thereof.

2. The metrology tool of claim 1, further comprising:
   viscoelastic layers embedded into structural materials of the metrology tool or into a supporting structure of the metrology tool.

3. The metrology tool of claim 1, further comprising:
   at least one particle or liquid impact damper in the metrology tool arranged to transmit vibratory energy into granular material or liquid of the damper for dissipation.

4. The metrology tool of claim 1, wherein the passive vibration isolation device isolates frequencies within a frequency range of 0.5 Hz to 150 Hz associated with a pedestal of the tool.

5. The metrology tool of claim 1, further comprising:
   at least one viscoelastic layer arranged to dampen vibrations within a frequency range of 50 Hz to 1 kHz and embedded in at least one of a tool bench and an optics supporting structure of the tool.

6. The metrology tool of claim 1, further comprising:
   at least one impact damper arranged to dampen vibrations within a frequency range of 1 kHz to 10 kHz and embedded within at least one of tool bench supports and a tool base table of the tool.

7. The metrology tool of claim 1, further comprising:
   an active isolation system configured to isolate vibration frequencies with a range of 2 Hz to 150 Hz.

8. The metrology tool of claim 1, further comprising:
   an active chuck leveler having sensor controlled actuators configured to maintain horizontal wafer position and minimize stage settling waiting time.

9. A method comprising:
   combining at least one active vibration isolation device and at least one passive vibration isolation device into a metrology tool, and,
   performing at least one step selected from a group consisting of:
   A) introducing constrained layer dampers and at least one particle or liquid impact damper into a supporting structure of the metrology tool;
   B) reducing mechanical frequencies by cancelling noise using at least one noise cancellation transducer;
   C) cancelling noise by detecting a vibration wave and generating an opposite wave having reversed polarity;
   D) combining at least one acoustic skin with at least one noise cancellation transducer configured to isolate the tool from acoustic vibrations in an environment of the tool;
   E) applying acoustic transducers to at least one of a tool base table and optics' supporting structures; and,
   F) combinations thereof.

10. The method of claim 9, further comprising:
    embedding viscoelastic layers into structural materials of the metrology tool or into a supporting structure of the metrology tool.

11. The method of claim 9, further comprising:
    transmitting vibratory energy using at least one particle or liquid impact damper in the metrology tool into granular material or liquid of the damper for dissipation.

12. The method of claim 9, further comprising:
    associating passive vibration isolation within a frequency range of 0.5 Hz to 150 Hz using a pedestal of the tool.

13. The method of claim 9, further comprising:
    embedding at least one viscoelastic layer arranged to dampen vibrations within a frequency range of 50 Hz to 1 kHz in at least one of a tool bench and an optics supporting structure of the tool.

14. The method of claim 9, further comprising:
    embedding at least one impact damper arranged to dampen vibrations within a frequency range of 1 kHz to 10 kHz within at least one of tool bench supports and a tool base table of the tool.

15. The method of claim 9, further comprising:
providing an active isolation system configured to handle vibration frequencies with a range of 2 Hz to 150 Hz.

16. The method of claim 9, further comprising:
providing an active chuck leveler having sensor controlled actuators configured to maintain horizontal wafer position and minimize stage settling waiting time.

\* \* \* \* \*

UNITED STATES PATENT AND TRADEMARK OFFICE
CERTIFICATE OF CORRECTION

| | | |
|---|---|---|
| PATENT NO. | : 9,546,946 B2 | Page 1 of 1 |
| APPLICATION NO. | : 14/361610 | |
| DATED | : January 17, 2017 | |
| INVENTOR(S) | : Golovanevsky et al. | |

It is certified that error appears in the above-identified patent and that said Letters Patent is hereby corrected as shown below:

On the Title Page

Item (54) and in the Specification, Column 1, Lines 1-2 the title of the invention which appears as "METROLOGY TARGET INDENTIFICATION, DESIGN AND VERIFICATION" should appear as --METROLOGY TARGET IDENTIFICATION, DESIGN AND VERIFICATION--.

Signed and Sealed this
Fourteenth Day of March, 2017

Michelle K. Lee
*Director of the United States Patent and Trademark Office*